US008496967B2

(12) United States Patent
Vladyka, Jr. et al.

(10) Patent No.: US 8,496,967 B2
(45) Date of Patent: Jul. 30, 2013

(54) ORAL FORMULATIONS

(75) Inventors: Ronald S. Vladyka, Jr., Somerset, NJ (US); David C. Dalgarno, Brookline, MA (US); John D. Iuliucci, Andover, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 476 days.

(21) Appl. No.: 12/655,180

(22) Filed: Dec. 23, 2009

(65) Prior Publication Data

US 2010/0247643 A1    Sep. 30, 2010

Related U.S. Application Data

(63) Continuation of application No. 11/985,094, filed on Nov. 14, 2007, now abandoned.

(60) Provisional application No. 60/858,870, filed on Nov. 14, 2006.

(51) Int. Cl.
*A61K 9/14* (2006.01)
*A61K 9/20* (2006.01)
*A61K 9/48* (2006.01)

(52) U.S. Cl.
USPC .................. 424/489; 424/452; 424/465

(58) Field of Classification Search
None
See application file for complete search history.

(56) References Cited

U.S. PATENT DOCUMENTS

| | | |
|---|---|---|
| 5,206,018 A | 4/1993 | Sehgal et al. |
| 5,234,456 A | 8/1993 | Silvestrini |
| 5,283,257 A | 2/1994 | Gregory et al. |
| 5,310,903 A | 5/1994 | Goulet et al. |
| 5,349,061 A | 9/1994 | Sinclair et al. |
| 5,378,696 A | 1/1995 | Caufield |
| 5,385,910 A | 1/1995 | Ocain et al. |
| 5,387,680 A | 2/1995 | Nelson |
| 5,391,730 A | 2/1995 | Skotnicki et al. |
| 5,434,260 A | 7/1995 | Skotnicki et al. |
| 5,464,650 A | 11/1995 | Berg et al. |
| 5,489,680 A | 2/1996 | Failli et al. |
| 5,491,231 A | 2/1996 | Nelson et al. |
| 5,516,781 A | 5/1996 | Morris et al. |
| 5,599,352 A | 2/1997 | Dinh et al. |
| 5,604,294 A | 2/1997 | Luly et al. |
| 5,660,873 A | 8/1997 | Nikolaychik et al. |
| 5,665,591 A | 9/1997 | Sonenshein et al. |
| 5,691,396 A | 11/1997 | Takemura et al. |
| 5,780,604 A | 7/1998 | Or et al. |
| 5,851,217 A | 12/1998 | Wolff et al. |
| 5,968,091 A | 10/1999 | Pinchuk et al. |
| 6,146,358 A | 11/2000 | Rowe |
| 6,152,141 A | 11/2000 | Stevens et al. |
| 6,153,252 A | 11/2000 | Hossainy et al. |
| 6,273,913 B1 | 8/2001 | Wright et al. |
| 6,340,734 B1 | 1/2002 | Lin et al. |
| 6,566,509 B1 | 5/2003 | Griffin et al. |
| 6,585,764 B2 | 7/2003 | Wright et al. |
| 6,803,171 B2 | 10/2004 | Gronbeck et al. |
| 7,091,213 B2 | 8/2006 | Metcalf, III et al. |
| 7,186,826 B2 | 3/2007 | Metcalf et al. |
| 2001/0007083 A1 | 7/2001 | Roorda |
| 2001/0010920 A1 | 8/2001 | Molnar-Kimber et al. |
| 2001/0027340 A1 | 10/2001 | Wright et al. |
| 2001/0029351 A1 | 10/2001 | Falotico et al. |
| 2001/0044651 A1 | 11/2001 | Steinke et al. |
| 2002/0016625 A1 | 2/2002 | Falotico et al. |
| 2002/0025495 A1 | 2/2002 | Ogata et al. |
| 2002/0031729 A1 | 3/2002 | Trefonas, III et al. |
| 2002/0195419 A1 | 12/2002 | Pavelchek |
| 2003/0033007 A1 | 2/2003 | Sirhan et al. |
| 2003/0170287 A1* | 9/2003 | Prescott ................. 424/423 |
| 2003/0209515 A1 | 11/2003 | Pavelchek |
| 2003/0220297 A1 | 11/2003 | Berstein et al. |
| 2004/0054186 A1 | 3/2004 | Das et al. |
| 2004/0073024 A1 | 4/2004 | Metcalf, III et al. |
| 2004/0077677 A1* | 4/2004 | Ashraf et al. ............ 514/291 |
| 2004/0254210 A1* | 12/2004 | Haeberlin et al. ....... 514/291 |
| 2005/0026868 A1 | 2/2005 | Metcalf, III et al. |
| 2005/0119288 A1 | 6/2005 | Bhattacharya et al. |
| 2006/0094745 A1* | 5/2006 | Ruffolo, Jr. ............. 514/291 |
| 2006/0183766 A1 | 8/2006 | Boni et al. |
| 2006/0264405 A1 | 11/2006 | Metcalf, III et al. |
| 2007/0004767 A1 | 1/2007 | Gutmann et al. |
| 2007/0036857 A1* | 2/2007 | Becker et al. ............ 424/470 |
| 2007/0105887 A1 | 5/2007 | Moore |

FOREIGN PATENT DOCUMENTS

| | | |
|---|---|---|
| JP | 63-090534 | 4/1988 |
| JP | 63-101427 | 5/1988 |
| JP | 08-143578 | 6/1996 |
| JP | 2001-051422 | 2/2001 |
| JP | 2001-053068 | 2/2001 |
| JP | 2002-40668 A | 2/2002 |
| JP | 2004-038143 | 2/2004 |

(Continued)

OTHER PUBLICATIONS

International Search Report for PCT/US07/23862 filed Nov. 14, 2007.
Abstract for JP 2001-053068.
Abstract for JP 2001-051422.
Abstract for JP 2002-040668.
Abstract for JP 2004-038143.
Abstract for JP 63-101427.
Abstract for JP 63-090534.
Abstract for JP 08-143578.
Bierer et al., "Cyclosporin A and FK506: molecular mechanisms of immunosuppression and probes for transplantation biology", Current Opinion in Immunology, 5:763-773, 1993.
Brazelton et al., "Molecular mechanisms of action of . . . mycophenolate mofetil and leflunomide", Current Opinion in Immunology, 8:710-720, 1996.
Chan et al., Phase II Study . . . Breast Cancer, Journal of Clinical Oncology, vol. 23, No. 23, pp. 5314-5322, 2005.
Chawla, Sant P. et al., "The Liddy Shriver Sarcoma Initiative", www.liddyshiversarcomainitiative.org, 2005, pp. 1-13.

(Continued)

*Primary Examiner* — Susan Tran

(74) *Attorney, Agent, or Firm* — Finnegan, Henderson, Farabow, Garrett & Dunner, LLP

(57) ABSTRACT

A solid pharmaceutical composition containing AP23573 suitable for oral administration is disclosed.

18 Claims, No Drawings

FOREIGN PATENT DOCUMENTS

| | | |
|---|---|---|
| JP | 2004-525950 A | 8/2004 |
| JP | 2008-514721 A | 5/2008 |
| WO | WO 90/13332 | 11/1990 |
| WO | WO 92/06992 | 4/1992 |
| WO | WO 94/04540 | 3/1994 |
| WO | WO 00/77575 A1 | 12/2000 |
| WO | WO 01/87263 A2 | 11/2001 |
| WO | WO 01/87342 A2 | 11/2001 |
| WO | WO 01/87373 A1 | 11/2001 |
| WO | WO 01/87374 A1 | 11/2001 |
| WO | WO 01/87375 A1 | 11/2001 |
| WO | WO 01/87376 A1 | 11/2001 |
| WO | WO 02/080975 | 10/2002 |
| WO | WO 02/091083 A1 | 11/2002 |
| WO | WO 03/064383 | 8/2003 |
| WO | WO 2005/034916 | 4/2005 |
| WO | WO 2005/034916 A1 | 4/2005 |
| WO | WO 2005/053661 | 6/2005 |
| WO | WO 2006/039414 | 4/2006 |
| WO | WO 2006/069038 | 6/2006 |
| WO | WO 2006/069038 A1 | 6/2006 |
| WO | WO 2006071966 A2 * | 7/2006 |

OTHER PUBLICATIONS

Dancey, Janet E., "Inhibitors of the mammalian target of rapamycin", *Expert Opinion Investig. Drugs*, 14(3):313-328, 2005.

De Scheerder et al., "Local methylprednisolone inhibition . . . intracoronary stents", Coronary Artery Disease, 7:161-166, 1996.

Dev et al, "Kinetics of drug delivery . . . nitinol stent", Catheterization and Cardiovascular Diagnosis, 34:272-278, 1995.

Gregory et al., "Treatment with rapamycin blocks arterial intimal thickening following mechanical and alloimmune injury", Transplantation Proceedings, 25:12-121, 1993.

Gregory et al., "Effects of treatment with cyclosporine, FK 506, rapamycin . . . in vitro and in vivo", Transplantation Proceedings, 25:770-771, 1993.

Gregory et al., "Rapamycin inhibits arterial intmal thickening caused by both alloimmune and mechanical injury", Transplantation, 55:1409-1418, 1993.

Hidalgo et al., A Phase I . . . Advanced Cancer, Clinical Cancer Research, 12(19), pp. 5755-5763, 2006.

Lambert et al., "Localized arterial wall drug delivery from a polymer-coated removable metallic stent", Circulation, 90:1003-1011, 1994.

Lincoff et al., "Sustained local delivery of dexamethasone . . . porcine coronary injury model", Journal of the American College of Cardiology, 29:808-816, 1997.

Marx et al., "Rapamycin-FKBP inhibits cell cycle regulators of proliferation in vascular smooth muscle cells", Clrculation Research, 76:412-417, 1995.

Mita et al., Phase I . . . advanced malignancies, Dev. Therapeutics: Mol. Therapeutics, Poster Session. vol. 22, 2004.

Morris et al., "Rapamycine (Sirolimus) Inhibits Vascular . . . Immune and Nonimmune Cells", Transplantation Proceedings, 27:430-431, 1995.

Ocain et al., "A Nonimmunosuppressive Triene-Modified Rapamycin . . . Cis-Trans Isomerase", Biochemical and Biophysical Research Communication, 192:1340-1346, 1993.

Raymond et al., Safety and Pharmacokinetics . . . With Cancer, Journal of Clinical Oncology, vol. 22, No. 12, pp. 2336-2347, 2004.

Sehgal, "Rapamune (Sirolimus, Rapamycin): An Overview and Mechanism of Action", Therapeutic Drug Monitoring, 17:660-665, 1995.

Thomson et al., "New Immunosuppressive Drugs: Mechanistic Insights and Potential Therapeutic Advances", Immunological Reviews, 136:71-98, 1993.

European Search Report dated Aug. 9, 2011 for European Application No. 06844354.8.

European Search Report dated Jul. 22, 2010 for European Application No. 06844354.8.

European Search Report dated May 4, 2006 for European Application No. 03735110.3.

Extended European Search Report dated Feb. 22, 2012 for European Application No. 11180546.1 filed Feb. 3, 2003.

Examination Report dated Dec. 20, 2010 in Australian Application No. 2009202913.

Examination Report dated Apr. 2, 2012 in Australian Application No. 2007319825.

Examination Report dated Sep. 28, 2011 in Australian Application No. 2006315512.

Examination Report dated Mar. 25, 2008 in Australian Application No. 2003210787.

Examination Report dated Nov. 9, 2010 in European Application No. 03735110.3.

Examination Report dated Apr. 17, 2012 in European Application No. 03735110.3.

International Search Report for PCT Application No. PCT/US07/023862 filed Nov. 14, 2007.

International Preliminary Report on Patentability and Written Opinion for PCT Application No. PCT/US07/023862 filed Nov. 14, 2007.

International Preliminary Report on Patentability and Written Opinion for PCT Application No. PCT/US06/044146 filed Nov. 14, 2006.

International Search Report for PCT Application No. PCT/US06/044146 filed Nov. 14, 2006.

International Search Report for PCT Application No. PCT/US03/03030 filed Feb. 3, 2003.

International Preliminary Examination Report for PCT Application No. PCT/US03/03030 filed Feb. 3, 2003.

Office Action dated Feb. 17, 2005 in U.S. Appl. No. 10/862,149.

Final Office Action dated Nov. 1, 2005 in U.S. Appl. No. 10/862,149.

Notice of Allowance dated Mar. 9, 2006 in U.S. Appl. No. 10/862,149.

Office Action dated May 6, 2008 in U.S. Appl. No. 11/650,017.

Office Action dated Jun. 29, 2009 in U.S. Appl. No. 11/650,017.

Notice of Allowance dated Dec. 15, 2009 in U.S. Appl. No. 11/650,017.

Notice of Allowance dated Oct. 19, 2006 in U.S. Appl. No. 11/494,418.

Office Action dated Apr. 6, 2007 in U.S. Appl. No. 10/537,152.

Office Action dated Feb. 17, 2005 in U.S. Appl. No. 10/635,054.

Office Action dated Apr. 25, 2012 in U.S. Appl. No. 12/655,180.

Office Action dated Sep. 22, 2010 in U.S. Appl. No. 12/798,501.

Notice of Allowance dated Jun. 29, 2011 in U.S. Appl. No. 12/798,501.

Restriction Requirement dated Oct. 10, 2007 in U.S. Appl. No. 11/598,850.

Office Action dated Jul. 18, 2008 in U.S. Appl. No. 11/598,850.

Office Action dated Apr. 27, 2009 in U.S. Appl. No. 11/598,850.

Office Action dated Oct. 11, 2011 in U.S. Appl. No. 11/598,850.

Final Office Action dated May 3, 2012 in U.S. Appl. No. 11/598,850.

Office Action dated Oct. 2, 2008 in U.S. Appl. No. 11/985,094.

Final Office Action dated Jun. 25, 2009 in U.S. Appl. No. 11/985,094.

Translation of Chinese Office Action dated Oct. 10, 2008 in Chinese Application No. 03807799.X.

Translation of Chinese Office Action dated Oct. 19, 2007 in Chinese Application No. 03807799.X.

Translation of Chinese Office Action dated Sep. 15, 2006 in Chinese Application No. 03807799.X.

Translation of Chinese Office Action dated Jan. 6, 2006 in Chinese Application No. 03807799.X.

Translation of Chinese Office Action dated May 4, 2012 in Chinese Application No. 200910149994.2.

Translation of Chinese Office Action dated Mar. 24, 2011 in Chinese Application No. 200780042435.0.

Translation of Chinese Office Action dated Mar. 18, 2010 in Chinese Application No. 200680051034.7.

Translation of Israeli Office Action dated Mar. 11, 2012 in Israeli Application No. 191356.

Translation of Israeli Office Action dated Jul. 4, 2011 in Israeli Application No. 198760.

Translation of Japanese Office Action dated Jan. 31, 2012 in Japanese Application No. 2008-540275.

* cited by examiner

ORAL FORMULATIONS

CROSS-REFERENCE TO RELATED APPLICATIONS

The present application is a continuation of and claims priority to U.S. Ser. No. 11/985,094, filed Nov. 14, 2007, and claims priority thereto and under 35 U.S.C. §119(e) to U.S. Provisional Patent Application No. 60/858,870, filed Nov. 14, 2006, the entire contents of which are hereby incorporated by reference.

BACKGROUND OF THE INVENTION

This invention relates to solid formulations of the 43-dimethylphosphinate ester of rapamycin (AP23573):

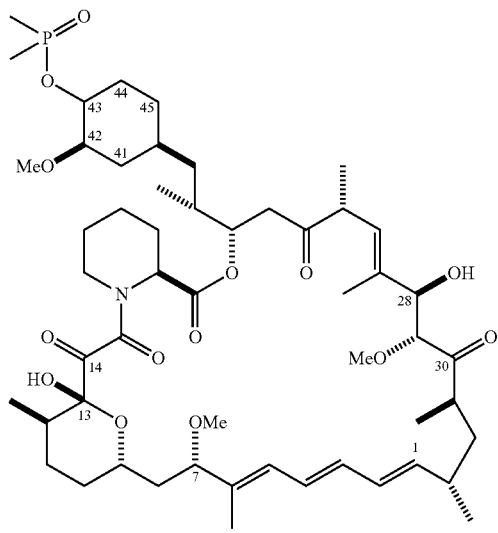

In in vitro and in vivo xenograft models, AP23573 has potently inhibited proliferation of a variety of human tumor cell lines, including prostate, endometrial, soft tissue and bone sarcoma, leukemia, lymphoma and glioblastoma cell lines.

Human clinical studies with AP23573 have yielded promising results in patients with various cancers, including possible delay in the time to progression or recurrence of tumors.

AP23573 is also in studies aimed at the development of AP23573-eluting stents. The role of AP23573 in that context is to inhibit restenosis following introduction of the stent.

Based in part on the known biological activities for other mTOR inhibitors, AP23573 may also be useful for a range of indications susceptible to treatment with an mTOR inhibitor, including without limitation, the treatment and prevention of organ transplant rejection and autoimmune diseases, fungal infection, multiple sclerosis; rheumatoid arthritis, systemic lupus erythematosus [see e.g., U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

One important challenge for the development and use of AP23573 is the development of storage stable solid dosage forms suitable for oral administration. More specifically, we have found that AP23573 tablets prepared by direct compression of non-micronized AP23573 with standard excipients and fillers, in the presence or absence of antioxidants, has thus far provided suboptimal tablets which did not exhibit desirably high homogeneity or stability.

SUMMARY OF THE INVENTION

We have made a detailed study of the degradation of AP23573 and have identified important degradation pathways involving the oxidation of the compound's triene moiety. In addition, we have found that AP23573 also undergoes aqueous degradation via cleavage of a lactone bond, resulting in the formation of the ring opened seco-AP23573.

Because AP23573 is an amorphous solid rather than a crystalline material like rapamycin or temsirolimus, we were unable to directly draw upon the reported experiences in formulating those compounds, and instead, relied upon empirical studies with AP23573 itself.

This invention, arising from those studies, overcomes the aforementioned problems and provides a reasonably storage stable, bioavailable oral formulation of AP23573, suitable for pharmaceutical use, without the need for micronization.

The pharmaceutical composition, suitable for oral administration, comprises 2-35% of AP23573, 0.01-3% of an antioxidant and 70-97% of a carrier material comprising at least one cellulose polymer, optionally containing one or more additional pharmaceutically acceptable excipients. Unless otherwise specified, all percentages in this document are on a weight/weight basis. Suitable carrier materials include microcrystalline cellulose, hydroxypropyl cellulose and lactose monohydrate, which can generally be used in amounts of 20-55%, 2-15% and 15-70%, respectively. A currently preferred antioxidant for use in this composition is butylated hydroxytoluene ("BHT"). Other excipients can include materials such as croscarmellose sodium and magnesium stearate.

The composition can be prepared in various physical forms (capsules, tablets, caplets, etc), and those containing 10-60 mg, typically 10-40 mg, of AP23573 are of greatest interest. Compressed tablets containing 10 mg of AP23573 are currently of greatest interest. The tablets may optionally contain a pharmaceutically acceptable film or enteric coating.

The composition can be prepared using otherwise conventional mixing technologies and apparatus, with wet granulation using a high shear type granulator followed by fluid bed drying being of greatest current interest.

In the process, a solution of AP23573 is provided in a selected solvent, e.g., an, aqueous ethanolic or aqueous solution (and other alcohols could be substituted for ethanol). The solution, which may also contain an antioxidant, is combined with the carrier to form a wet mass. This is typically carried out in a granulator or other mixing apparatus, e.g., a high shear granulator. The wet mass is then mixed, e.g. by granulation, to generate wet granules. The wet granules are then dried, e.g., in a fluid bed drier, to generate dried granules, which can be compressed into tablets and coated as desired.

As noted above, the solution of AP23573 can also contain an antioxidant. Alternatively, or in addition, an antioxidant can be separately combined with the carrier material before or after addition of the solution of AP23573, in any event, being incorporated in the resultant wet mass. Other excipients may also be added at that step for incorporation into the wet mass. Excipients can also be added to the wet or dry granules as well.

The solid pharmaceutical composition prepared by this method has been found to possess suitable storage stability and bioavailability for use in human clinical studies.

DETAILED DESCRIPTION OF THE INVENTION

This invention provides a storage stable, solid pharmaceutical composition in unit dosage form which comprises AP23573, an antioxidant and a cellulose polymer. The composition may also contain one or more other pharmaceutically acceptable excipients such as chelating agents, fillers, binders, surfactants, disintegrants, lubricants, pH modifying agents and the like. It is prepared using a wet granulation process as described above.

Suitable solvents for preparing the solution of AP23573 and for possible use in the granulation step include but are not limited to water and organic solvents (e.g., methanol, ethanol, isopropyl, acetone) either alone or in combination. It is preferred that the wet granulation be performed with an alcoholic solvent system in which ethanol is currently of greatest interest as the alcohol. Aqueous ethanol is an example of a combination granulation solvent system that includes water and ethanol together.

It is currently of particular interest that the composition contain from 1 to 45%, from 2 to 35%, from 5 to 25%, or from 8 to 15% by weight of AP23573; from 1 to 50%, from 1 to 35%, from 1 to 15%, or from 2 to 15% by weight of cellulose polymer and from 0.01% to 3%, from 0.05% to 1% or from 0.05% to 0.5% by weight of antioxidant. However, various embodiments may contain more, or less, of these components.

Acceptable antioxidants include, but are not limited to, citric acid, d,l-α-tocopherol, BHA, BHT, monothioglycerol, ascorbic acid, and propyl gallate. It is expected that the antioxidants of the formulations of this invention will be used in amounts ranging from 0.01% to 3% wt/wt relative to the weight of the tablet.

A chelating agent, or other material capable of binding metal ions, such as ethylene diamine tetra acetic acid (EDTA) and its salts, are capable of enhancing the stability of AP23573 and may be used as an optional excipient.

Typical cellulose polymers include, but are not limited to hydroxypropylmethylcellulose (HPMC), hydroxypropylmethyl cellulose phthalate, methyl cellulose (MC), hydroxyethyl cellulose, and hydroxypropyl cellulose (HPC). Other pharmaceutically acceptable cellulosic polymers are mentioned herein in various contexts and many others are well known in the art.

Pharmaceutically acceptable excipients include binders, fillers, disintegrants, pH modifying agents, surfactants, and any combinations of the foregoing.

Acceptable pH modifying agents include, but are not limited to, citric acid, sodium citrate, dilute HCl, and other mild acids or bases capable of buffering a solution containing AP23573 to a pH in the range of about 4 to about 6. If present in the composition, the pH modifying agent is usually in amount of up to 1% by weight relative to the weight of the tablet.

Surfactants may be present in the formulation and include polysorbate 80, sodium lauryl sulfate, sodium dodecyl sulfate, salts of bile acids (taurocholate, glycocholate, cholate, deoxycholate, etc.) which may be combined with lecithin. Alternatively, ethoxylated vegetable oils, such as Cremophor EL, vitamin E tocopherol propylene glycol succinate (Vitamin E TGPS), polyoxyethylene-polyoxypropylene block copolymers, and poloxamers. If present in the composition, the surfactant is usually in amount of up to 20%, for example 1 to 15% by weight relative to the weight of the tablet.

Binders, fillers, and disintegrants such as sucrose, lactose, microcrystalline cellulose, croscarmellose sodium, magnesium stearate, gum acacia, cholesterol, tragacanth, stearic acid, gelatin, casein, lecithin (phosphatides), carboxymethylcellulose calcium, carboxymethylcellulose sodium, methylcellulose, hydroxyethylcellulose, hydroxypropylcellulose, hydroxypropylmethycellulose phthalate, noncrystalline cellulose, polyvinylpyrrolidone, cetostearyl alcohol, cetyl alcohol, cetyl esters wax, dextrates, dextrin, cyclodextrin, lactose, dextrose, glyceryl monooleate, glyceryl monostearate, glyceryl palm itostearate, polyoxyethylene alkyl ethers, polyethylene glycols, polyoxyethylene castor oil derivatives, polyoxyethylene stearates, and polyvinyl alcohol, and the like may also be incorporated into the formulation.

Any given formulation of this invention may contain multiple ingredients of each class of component. For example, a formulation containing an antioxidant may contain one or more antioxidants as the antioxidant component.

In an exemplary embodiment, the wet granulation process includes the steps of mixing, wetting, wet massing, granulating, drying and sieving. The steps are discussed in more detail below.

The wet granulation process begins with the preparation of a solution comprising AP23573 and an antioxidant. Suitable solvents include water, methanol, ethanol, isopropanol, and the like, where ethanol is of particular interest. The next step is adding the solution to a mixer containing a "matrix forming material" and one or more optional intragranular excipients, while agitating the contents of the mixer, resulting in the formation of a wet mass. This step is also called wet massing the powder intragranular blend. Examples of suitable matrix forming materials include a cellulose polymer, and also comprise binders and fillers to promote dissolution enhancement of the final product. Typical intragranular excipients may include binders, fillers, disintegrants and any combinations of the foregoing. An example of cellulose polymer/intragranular excipient mixture includes but is not limited to, a combination of microcrystalline cellulose, lactose monohydrate, croscarmellose sodium and hydroxypropyl cellulose. The wet mass is then granulated in the mixer, generating a mixture of the various ingredients in the form of wet granules. The granulation (i.e., mixing/agitation) is continued until a uniform granulation is achieved (i.e., until the particle sizes of the granules reach a desired uniformity). The mixer can be a blender with intensifying bar, a low shear granulator or a high shear granulator. The wet granules are then dried, e.g., in a fluid bed dryer at temperature between 45 and 55° C. The dried granular material may then be milled using a suitable milling device, such as a Fitz mill. The wet granulation and drying can be done in a fluid bed granulator/dryer. The wet granules can be dried using a tray drying oven. After they are dried, the granules can be further sieved, i.e., dry screened, alone or in combination with one or more additional excipients. Also, if desired, the dried granules can be further blended with extragranular fillers and binders, such as microcrystalline cellulose, croscarmellose sodium, and magnesium stearate in a blender such as a V-blender. This typically results in a more uniform particle size of the granules, which may then be compressed into tablets.

In an alternative process, the solution of AP23573 does not contain an antioxidant. In this approach, the antioxidant is instead present among the contents of the mixer, which contents also include the cellulose polymer, intragranular excipients etc.

In other embodiments, the antioxidant is again present in the mixer containing the cellulose polymer and intragranular excipients, and AP23573 is added as a solid and then mixed with the intragranular excipients. The solvent is then added to the mixer prior to the granulation step. Other sequences of addition are possible and permissible under this invention.

The oral tablet may further comprise a film-coat to control the release of AP23573. The tablet may be coated with a film-coat by spraying, dipping or by deposition using various coating solvents. Suitable coating solvents include water, methanol, ethanol, isopropanol, and the like. The film-coat includes a polymeric film-forming material such as copovidone (i.e a copolymer of polyvinylpyrrolidone and vinyl acetate), hydroxypropyl methylcellulose, hydroxypropylcellulose, and acrylate or methacrylate copolymers. Besides a film-forming polymer, the film-coat may further comprise a plasticizer, e.g. polyethylene glycol, triethyl citrate, a surfactant, e.g. a Tween® type, an antifoaming agent, e.g. simethicone, and optionally a pigment, e.g. titanium dioxide or iron oxides. The film-coating may also comprise talc as anti-adhesive. The film coat usually accounts for less than about 5% by weight of the dosage form.

In a preferred embodiment, the film-coating material comprises copovidone, which allows for rapid release of AP23573.

The film coating may also be an enteric layer comprising an enteric polymer, for delayed release of AP23573. An enteric layer is a coating of a substance (i.e a polymer) which is insoluble in the acid medium of the stomach but which is soluble at the higher pH encountered in the intestine. Such materials are used as film coatings on tablets to modify the release of a drug. Suitable enteric polymers are well known to those of skill in the art (WO 01/051031) and include, without limitation, methyl metacrylate polymers, methacrylic acid co-polymers, cellulose acetate phthalate, polyvinyacetate phthalate, hydroxypropyl methyl phthalate, and hydroxypropyl methyl cellulose phthalate. The enteric-coat may also further comprise a plasticizer, a surfactant, and anti foaming agent and optionally a pigment as previously described.

In a preferred embodiment, the enteric layer comprises methacrylic acid co-polymer, e.g. Eudragit L100, Acryl-EZE and the like.

The following provide representative examples of the formulations of this invention. The preparation of AP23573 is described in U.S. Pat. No. 7,091,213 which is hereby incorporated by reference. These examples are illustrative only, and do not serve to limit the scope of the invention described herein. The examples are meant only to suggest a method of practicing the present invention.

EXAMPLES

Example 1

Alcoholic Granulation

Core Tablets

The following procedure was used to prepare a tablet containing 10 mg of AP23573 containing the ingredients listed below. The tablets are 6 mm diameter, white to off-white, round, biconvex, coated tablets. The composition of the core tablet is shown in the following table. In this example, core tablets are film-coated and may be used as such, or may be enteric-coated for delayed release.

| Component | Weight Percent |
|---|---|
| AP23573 | 8.00% |
| Butylated Hydroxytoluene | 0.08% |
| Hydroxy Propyl Cellulose | 8.00% |
| Lactose Monohydrate | 50.57% |
| Microcrystalline Cellulose | 30.85% |
| Croscarmellose Sodium | 2.00% |
| Magnesium Sterate | 0.50% |
| Dehydrated Alcohol (Ethanol)* | — |

*Removed during processing

Process

Hydroxypropyl Cellulose, Lactose Monohydrate, Microcrystalline Cellulose, and half of the Croscarmellose Sodium, were mixed in a high shear granulator. The AP23573 and Butylated Hydroxytoluene (BHT) were dissolved in Dehydrated Alcohol, USP, mixing not less than 45 minutes. The solution of AP23573 and BHT was added to the granulator and mixed to a wet mass for approximately 3 minutes.

The granulated mixture was dried in a fluid bed dryer at 45-55° C. for 60-90 minutes, after which the dried granulated material was passed through a mill fitted with a 0.045-inch screen opening to remove oversized material. The milled granulated material was then added to a V-blender and blended with Magnesium Stearate, NF and the remaining half of the Croscarmellose Sodium, NF until uniformly blended.

The granulated material was pressed into tablets using a tablet press set up with 6 mm round concave tooling. The press was adjusted as required for a target tablet weight of 125.0 mg, hardness of 5.5 kp, friability no more than 1%, and disintegration time less than 10 minutes.

Film Coating

The film coating was prepared according to following procedure using the following components.

| Film Coating | Percent of Solution |
|---|---|
| Copovidone | 20.00% |
| Dehydrated Alcohol (Ethanol)* | 80.00% |

*Removed during processing

The tablets were added to a coating pan and were coated with a solution of Copovidone in Dehydrated Alcohol, USP, maintaining a product temperature of 20-35° C., until a weight gain of 5% is achieved. The pan was then cooled and the film-coated tablets were allowed to dry. Film-coated tablets may be packaged as such, or may be enteric coated.

Enteric Coating

The enteric coating was prepared according to following procedure using the following components.

| Film Coating | Percent of Suspension |
|---|---|
| Methacrylic Acid Co-polymer | 11.03% |
| Triethyl Citrate | 2.16% |
| Talc | 2.81% |
| Dehydrated Alcohol (Ethanol)* | 84.00% |

*Removed during processing

For enteric coating, the tablets are placed in a coating pan and coated with a suspension of Methacrylic Acid Copolymer, NF, Triethyl Citrate, NF, and Talc in Dehydrated Alcohol, USP, maintaining a product temperature of 20-35° C., until a weight gain of 8% is achieved. The pan was then cooled, and the enteric-coated tablets were allowed to dry.

Example 2

Aqueous Granulation

Core Tablets

The following procedure was used to prepare a tablet containing 50 mg of AP23573 containing the ingredients listed below. The composition of the core tablet is shown in the following table. Core tablets are film-coated and may be used as such, or may be enteric-coated.

| Component | Weight Percent |
| --- | --- |
| AP23573 | 25.00% |
| Butylated Hydroxytoluene | 0.20% |
| Hydroxy Propyl Cellulose | 4.00% |
| Lactose Monohydrate | 23.75% |
| Microcrystalline Cellulose | 43.55% |
| Croscarmellose Sodium | 3.00% |
| Magnesium Stereate | 0.50% |
| DI Water* | — |

*Removed during processing

Butylated Hydroxytoluene (BHT) was passed through a mill fitted with a 0.010 screen and was mixed with Hydroxypropyl Cellulose, half of the Microcrystalline Cellulose, and one third of Croscarmellose Sodium in a high shear granulator. The AP23573 was then added to the granulator and mixed for 5 minutes. The granulation process was then begun while adding the granulation fluid (deionized water) over 5 minutes. The AP23573, BHT and excipients were mixed to a wet mass for approximately 2 minutes.

The granulated mixture was dried in a fluid bed dryer at 45-55° C. for 60-90 minutes, after which the dried granulated material was passed through a mill fitted with a 0.065-inch screen opening to remove oversized material. The milled granulated material was then blended with Magnesium Stearate, the remaining two thirds of Croscarmellose Sodium and the remaining half of microcrystalline cellulose.

The granulated mixture was pressed into tablets using a tablet press set up with 6 mm round concave tooling. The press was adjusted as required for a target tablet weight of 200.0 mg, hardness of 8.5 kp, friability no more than 1%, and disintegration time less than 10 minutes.

Film Coating

The film coating was prepared according to following procedure using the following components.

| Film Coating | Percent of Solution |
| --- | --- |
| Copovidone | 7.00% |
| DI Water* | 93.00% |

*Use Removed during processing

The tablets were added to a coating pan and were coated with a solution of Copovidone in Deionized water, maintaining a product temperature of 27-31° C., until a weight gain of 2% is achieved. The pan was then cooled and the film-coated tablets were allowed to dry. Film-coated tablets may be packaged as such, or may be enteric coated.

Enteric Coating

The enteric coating was prepared according to following procedure using the following components.

| Film Coating | Percent of Suspension |
| --- | --- |
| Methacrylic Acid Co-polymer | 9.94% |
| Simethicone | 0.06% |
| DI Water* | 90.00% |

*Removed during processing

For enteric coating, the tablets are placed in a coating pan. The Simethicone was dispersed in deionized water using vigorous mixing to make a 10% final coating solution. The Methacrylic Acid Co-polymer was then added and mixed to the Simethicone/water mixture. The coating pan and tablets were warmed up to a product temperature of 30 to 33° C. The coating solution was sprayed onto the tablet until a weight gain of 10% is achieved. The pan was then cooled, and the enteric-coated tablets were allowed to dry.

The documents cited throughout the specification are hereby incorporated by reference. Minor variations and modifications to the methods and materials set forth in the foregoing detailed description and illustrative examples will be readily apparent to those of skill in the art and are encompassed within the scope of the invention.

The invention claimed is:

1. A solid composition, comprising:
8.00% by weight of 43-dimethylphosphinate ester of rapamycin with the following structure,

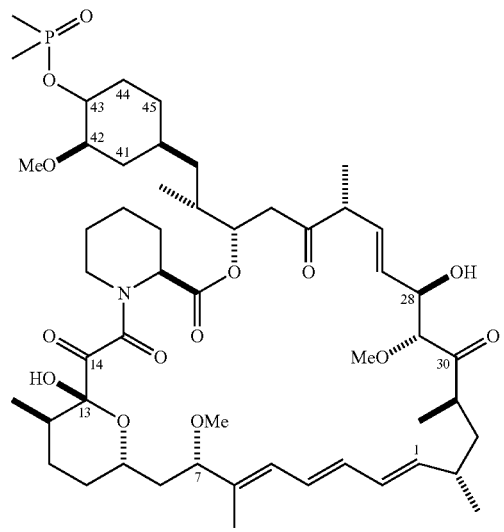

(AP23573)

0.08% by weight of an antioxidant;
8.00% by weight of hydroxypropyl cellulose;
50.57% by weight of lactose monohydrate;
30.85% by weight of microcrystalline cellulose;
2.00% by weight of croscarmellose sodium; and
0.5% by weight of magnesium stearate.

2. The solid composition of claim 1, wherein the antioxidant comprises butylated hydroxytoluene.

3. The solid composition of claim 1, further comprising a film coating.

4. The solid composition of claim 3, wherein the film coating comprises copovidone.

5. The solid composition of claim 1 or claim 3, further comprising an enteric coating.

6. The solid composition of claim 5, wherein the enteric coating comprises methacrylic acid copolymer, triethyl citrate, and talc.

7. A process for preparing a solid pharmaceutical composition of claim 1, comprising:
   (a) providing a solution of comprising AP23573 in a solvent;
   (b) combining the solution with the at least one carrier to form a wet mass;
   (c) granulating the wet mass to generate wet granules;
   (d) drying the wet granules to generate dried granules; and
   (e) compressing the dried granules into tablets;
   wherein
   the solution in step (a) further comprises at least one antioxidant, or the carrier in step (b) is combined with at least one antioxidant prior to combining with the solution of comprising AP23573.

8. The process of claim 7, wherein step (b) further comprises combining at least one pharmaceutically acceptable excipient with the solution and the at least one carrier to form a wet mass.

9. The process of either of claim 7 or 8, wherein at least one additional pharmaceutically acceptable excipient is added to the granules before or after drying in step (d).

10. The process of claim 9, wherein the at least one additional pharmaceutically acceptable excipient is selected from croscarmellose sodium, magnesium stearate, and combinations or mixtures thereof.

11. A solid pharmaceutical composition prepared by the method of claim 7 or claim 8.

12. The solid pharmaceutical composition of claim 11, wherein AP23573 is present in an amount ranging from about 10 mg to about 40 mg.

13. The process of claim 7, further comprising the step of:
   (f) coating the tablets with a coating.

14. A solid pharmaceutical composition prepared by the method of claim 9.

15. The solid pharmaceutical composition of claim 14, wherein the solid dosage form comprises 10 mg of AP23573.

16. A solid pharmaceutical composition prepared by the method of claim 10.

17. The solid pharmaceutical composition of claim 16, wherein the solid dosage form comprises 10 mg of AP23573.

18. The solid pharmaceutical composition of claim 11, wherein the solid dosage form comprises 10 mg of AP23573.

* * * * *